United States Patent
Kanno et al.

(10) Patent No.: US 9,498,549 B2
(45) Date of Patent: Nov. 22, 2016

(54) STERILIZATION METHOD AND STERILIZATION PROCESSING APPARATUS

(75) Inventors: Minoru Kanno, Sendai (JP); Masahiro Kohno, Sendai (JP); Atsuo Iwasawa, Sendai (JP); Takayuki Mokudai, Sendai (JP)

(73) Assignee: MINORU KANNO, Sendai-Shi (JP)

( * ) Notice: Subject to any disclaimer, the term of this patent is extended or adjusted under 35 U.S.C. 154(b) by 1459 days.

(21) Appl. No.: 11/992,590

(22) PCT Filed: Aug. 24, 2007

(86) PCT No.: PCT/JP2007/066426
§ 371 (c)(1),
(2), (4) Date: Mar. 26, 2008

(87) PCT Pub. No.: WO2008/032544
PCT Pub. Date: Mar. 20, 2008

(65) Prior Publication Data
US 2009/0148341 A1    Jun. 11, 2009

(30) Foreign Application Priority Data
Sep. 15, 2006  (JP) .................................. 2006-251746

(51) Int. Cl.
*A61L 2/03* (2006.01)
*A61L 2/16* (2006.01)
(Continued)

(52) U.S. Cl.
CPC .................. *A61L 2/035* (2013.01); *A61L 2/16* (2013.01); *B08B 3/08* (2013.01); *C02F 1/4674* (2013.01); *C02F 2001/46185* (2013.01)

(58) Field of Classification Search
CPC ........... A61L 2/035; A61L 2/16; B08B 3/08; C02F 1/4674; C02F 2001/46185
USPC ........ 422/29, 31, 33, 37; 204/242, 246, 247, 204/258, 265, 266; 261/30–32, 54, 65, 77, 261/133, 151, 161
See application file for complete search history.

(56) References Cited

U.S. PATENT DOCUMENTS 5,932,171 A *  8/1999  Malchesky .................... 422/29
6,398,928 B1 *  6/2002  Koganezawa et al. ....... 204/262
(Continued)

FOREIGN PATENT DOCUMENTS

DE   100 51 180 A1   8/2002
JP   A 02-111708     4/1990
(Continued)

OTHER PUBLICATIONS

Jun. 18, 2010 Supplementary European Search Report issued in European Patent Application No. 07 80 6033.

*Primary Examiner* — Timothy Cleveland
(74) *Attorney, Agent, or Firm* — Oliff PLC

(57) ABSTRACT

A sterilization method and sterilization processing apparatus having a high sterilization effect and capable of shortening a sterilization time are provided. An electrolysis apparatus 2 electrolyzes water in a reservoir 1 and generates strongly acidic electrolytic water in an anode chamber 11 and generates strongly alkaline electrolytic water in a cathode chamber 12. A first wash container 3 is provided with a drain having an on-off valve and retains the strongly alkaline electrolytic water in the cathode chamber 12. A second wash container 4 is hermetically sealable, provided with a drain having an on-off valve and retains the strongly acidic electrolytic water of the anode chamber 11. A gas jetting apparatus 5 has a collector pipe 51 communicating with the inside of the second wash container 4 and causes air or a chlorine gas collected from the inside of the second wash container 4 through the collector pipe 51 to jet in the strongly acidic electrolytic water inside the second wash container 4. A waste water container 6 receives waste water from a drain 31 of the first wash container 3 and a drain 41 of the second wash container 4.

12 Claims, 3 Drawing Sheets

(51) Int. Cl.
*B08B 3/08* (2006.01)
*C02F 1/467* (2006.01)
*C02F 1/461* (2006.01)

(56) References Cited

U.S. PATENT DOCUMENTS

2004/0045836 A1* 3/2004 Tseng .................. 205/620
2007/0205522 A1* 9/2007 Dulphy et al. .................. 261/65

FOREIGN PATENT DOCUMENTS

| | | | |
|---|---|---|---|
| JP | A | 08-308910 | 11/1996 |
| JP | U | 3035658 | 1/1997 |
| JP | A | 09-028769 | 2/1997 |
| JP | A | 10-118003 | 5/1998 |
| JP | A | 10-137762 | 5/1998 |

* cited by examiner

FIG.1
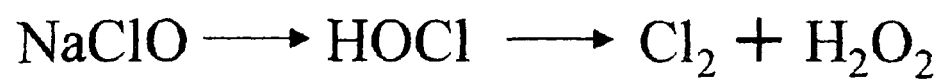
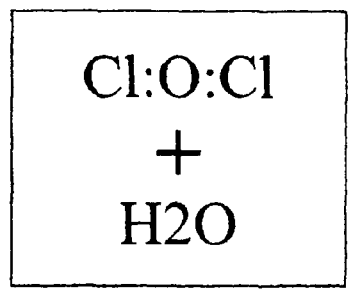
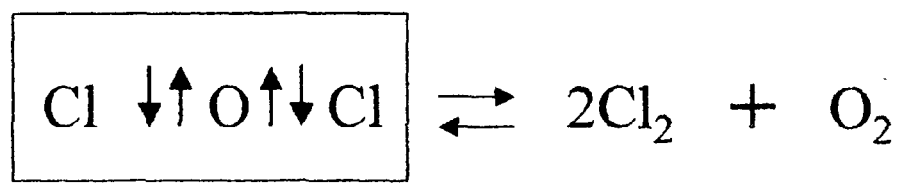
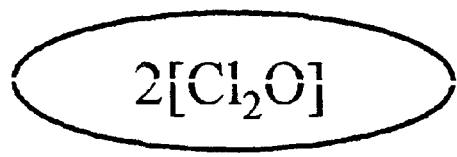

STERILIZATION METHOD AND STERILIZATION PROCESSING APPARATUS

BACKGROUND OF THE INVENTION

Field of the Invention

The present invention relates to a sterilization method and sterilization processing apparatus.

Description of the Related Art

Conventionally, there are apparatuses which retain water with hydrochloric acid and salt in a cathode chamber and an anode chamber of an electrolyte cell and generate sterilizing water containing hypochlorous acid of less than pH 3 through electrolysis (see Japanese Patent Laid-Open No. 10-137762, for example).

However, the conventional sterilizing water obtained through electrolysis from water with hydrochloric acid and salt has no difference from an aqueous solution of hypochlorous acid which can be manufactured by mixing hypochlorous acid and diluted hydrochloric acid and has no difference in sterilizing power either. Moreover, even when compared with an aqueous solution of sodium hypochlorite which is normally used, no advantages of using electrolytic water are found except in that the amount of chlorine gas exhausted is small.

The present invention has been implemented by focusing attention on the above described conventional problems and it is an object of the present invention to provide a sterilization method and sterilization processing apparatus having a high sterilization effect and capable of shortening a sterilization time.

SUMMARY OF THE INVENTION

Sterilization action of acidic electrolytic water has been conventionally considered as action by hydroxyl radical which is generated in a process of decomposition of a trace quantity of hydrogen peroxide and high concentration of hypochlorous acid that exist in an acidic aqueous solution. However, the amount of hydroxyl radical generated from hypochlorous acid is minimal and effective sterilization cannot be achieved. Moreover, since hydroxyl radicals generated once react with each other and produce hydrogen peroxide, there is another problem of reducing sterilizing power. An aqueous solution of hypochlorous acid alone is not sufficient to realize especially cleaning and sterilization of medical equipment in general.

The inventor of the present invention has brought the present invention to perfection by discovering that it is possible to obtain a high sterilization effect by electrolyzing a saline solution, thereby generating acidic electrolytic water with high concentration of effective chlorine, soaking an object to be treated in strongly acidic electrolytic water and causing air to jet (aerate). The inventor has discovered that the ratio of reduction of effective chlorine and dissolved oxygen in water due to aeration processing is 2:1 in a molar ratio in this strongly acidic electrolytic water. Based on this knowledge, the inventor has concluded that unknown matter composed of effective chlorine and dissolved oxygen bonded together at a molar ratio of 2:1, that is chlorine/oxygen adducts are dissolved in strongly acidic electrolytic water.

That is, strongly acidic electrolytic water according to the present invention features the inclusion of chlorine/oxygen adducts composed of effective chlorine and dissolved oxygen bonded together at a molar ratio of 2:1.

The strongly acidic electrolytic water according to the present invention preferably has pH within a range of 2 to 4.

The strongly acidic electrolytic water according to the present invention can be generated by electrolyzing an aqueous solution of chloride. The aqueous solution of chloride is preferably composed of an aqueous solution of salt, aqueous solution of potassium chloride, aqueous solution of hydrochloric acid or an aqueous solution of a mixture of two or more kinds of these aqueous solutions and is more preferably composed of saline solution. The strongly acidic electrolytic water according to the present invention preferably has concentration of effective chlorine of 20 to 120 ppm.

The strongly acidic electrolytic water according to the present invention can be obtained by electrolyzing a saline solution of 10 mM concentration at a voltage of 12 V and a current of 0.8 A for 15 minutes. The reaction process thereof is shown in FIG. 1.

The strongly acidic electrolytic water according to the present invention has a high sterilization effect by jetting or stirring a gas.

To confirm that chlorine/oxygen adducts dissolved in the strongly acidic electrolytic water is composed of effective chlorine and dissolved oxygen at a molar ratio of 2:1, the following testing was conducted.

First, a 10 mM saline solution was subjected to electrolysis using an electrolysis apparatus with a diaphragm at a voltage of 12 V and a current of 0.8 A, and strongly acidic electrolytic water of pH 2.45 was generated. 300 mL of the strongly acidic electrolytic water generated was put in a beaker, continuously stirred by a stirrer and effective chlorine (Cl) in water, dissolved oxygen (DO), electric conductivity (EC), pH, oxidation and reduction potential (ORP) and water temperature (WT) were measured. The result is shown in Table 1. Furthermore, instead of continuing to stir using a stirrer, air was sent at a rate of 10 L/minute using an air pump to cause the air to jet in the strongly acidic electrolytic water and effective chlorine (Cl) and dissolved oxygen (DO) in water were measured. The result is shown in Table 2 and FIG. 2. Furthermore, stirring using a stirrer and jetting of air at a rate of 10 L/minute using an air pump were conducted to measure effective chlorine (Cl) in water, dissolved oxygen (DO), electric conductivity (EC), pH, oxidation and reduction potential (ORP), water temperature (WT). The result is shown in Table 3.

TABLE 1

| Time(minutes) | Cl mg/L | DO mg/L | DH ppb | ORP mV | EC mS/cm | pH |
|---|---|---|---|---|---|---|
| 0 | 105 | 19.40 | 0.50 | 1144 | 2.45 | 2.26 |
| 1 | 100 | 17.36 | 0.69 | 1159 | 2.40 | 2.18 |
| 2 | 92 | 16.22 | 0.43 | 1159 | 2.34 | 2.17 |
| 3 | 87 | 15.48 | 0.46 | 1154 | 2.26 | 2.15 |
| 4 | 84 | 14.86 | 0.43 | 1158 | 2.34 | 2.18 |
| 5 | 79 | 13.54 | 0.20 | 1158 | 2.27 | 2.21 |
| 6 | 74 | 12.66 | 0.15 | 1158 | 2.32 | 2.22 |
| 7 | 72 | 11.82 | 0.14 | 1155 | 2.17 | 2.25 |
| 8 | 67 | 10.46 | 0.06 | 1155 | 2.05 | 2.20 |
| 9 | 63 | 10.28 | 0.03 | 1153 | 2.03 | 2.24 |
| 10 | 59 | 9.81 | 0.00 | 1152 | 2.08 | 2.21 |

TABLE 2

| Time(minutes) | DO mg/L | Cl mg/l | O₂ mM | Cl₂ mM |
| --- | --- | --- | --- | --- |
| 0 | 15.59 | 117 | 0.49 | 1.65 |
| 1 | 11.24 | 97 | 0.35 | 1.37 |
| 2 | 9.42 | 85 | 0.29 | 1.20 |
| 3 | 8.74 | 79 | 0.27 | 1.11 |
| 4 | 8.37 | 71 | 0.26 | 1.00 |
| 5 | 8.28 | 63 | 0.26 | 0.89 |
| 6 | 8.35 | 55 | 0.26 | 0.77 |
| 10 | 8.13 | 44 | 0.25 | 0.62 |
| 20 | 7.97 | 24 | 0.25 | 0.34 |
| 30 | 8.00 | 15 | 0.25 | 0.21 |
| 40 | 8.03 | 9 | 0.25 | 0.13 |

TABLE 3

| Time(minutes) | Cl mg/L | DO mg/L | DH ppb | ORP mV | EC mS/cm | pH |
| --- | --- | --- | --- | --- | --- | --- |
| 0 | 105 | 19.40 | 0.50 | 1144 | 2.45 | 2.26 |
| 1 | 98 | 13.40 | 0.20 | 1150 | 2.38 | 2.18 |
| 2 | 92 | 10.14 | 0.03 | 1151 | 2.34 | 2.24 |
| 3 | 83 | 8.98 | 0.00 | 1154 | 2.23 | 2.20 |
| 4 | 74 | 8.48 | 0.00 | 1149 | 2.26 | 2.25 |
| 5 | 67 | 8.30 | 0.00 | 1150 | 2.15 | 2.25 |
| 6 | 57 | 8.20 | 0.00 | 1149 | 2.20 | 2.23 |
| 7 | 52 | 8.29 | 0.00 | 1148 | 2.10 | 2.23 |
| 8 | 50 | 8.30 | 0.00 | 1147 | 2.16 | 2.24 |
| 9 | 44 | 8.37 | 0.00 | 1144 | 2.07 | 2.25 |
| 10 | 39 | 8.54 | 0.00 | 1142 | 2.04 | 2.26 |

It is appreciated from Table 2 that while effective chlorine was reduced by 0.28 mM for one minute after electrolysis started, dissolved oxygen was reduced by 14 mM, half that of the above described case. It is possible to draw an inference from these results that the strongly acidic electrolytic water contains chlorine/oxygen adducts composed of effective chlorine and dissolved oxygen bonded together at a molar ratio of 2:1, which was gasified by jetting (aeration) of gas in strongly acidic electrolytic water in an extremely short time and exhausted from strongly acidic electrolytic water.

A first sterilization method according to the present invention is characterized by soaking an object to be treated in strongly acidic electrolytic water of pH 2 to 4 obtained by electrolyzing an aqueous solution of chloride and causing air to jet in the strongly acidic electrolytic water, collecting a chlorine gas exhausted from the strongly acidic electrolytic water and causing the collected chlorine gas to jet inside the strongly acidic electrolytic water.

In the first sterilization method according to the present invention, the aqueous solution of chloride is preferably composed of an aqueous solution of salt, aqueous solution of potassium chloride, aqueous solution of hydrochloric acid or aqueous solution of a mixture of two or more kinds of these aqueous solutions and more preferably composed of a salt aqueous solution.

The first sterilization method according to the present invention has a high sterilization effect by causing the gas to jet in the strongly acidic electrolytic water.

A second sterilization method according to the present invention is characterized by soaking an object to be treated in strongly acidic electrolytic water of pH 2 to 4 obtained by electrolyzing an aqueous solution of chloride, stirring the aqueous solution of chloride, collecting a chlorine gas exhausted from the strongly acidic electrolytic water and causing the collected chlorine gas to jet in the strongly acidic electrolytic water. The strongly acidic electrolytic water may also be stirred using ultrasonic wave in addition to using a stirrer. When ultrasonic wave is used, the strongly acidic electrolytic water can be stirred with cavitation generated by ultrasonic wave. The stirring using ultrasonic wave can be conducted using an ultrasonic wave generator. The frequency of ultrasonic wave is preferably 20 kHz to 50 kHz, but the frequency is not limited to such a range.

The second sterilization method according to the present invention has a high sterilization effect by stirring.

A third sterilization method according to the present invention is characterized by including a first step of electrolyzing an aqueous solution of chloride and generating strongly acidic electrolytic water and strongly alkaline electrolytic water, a second step of cleaning the object to be treated with the strongly alkaline electrolytic water obtained in the first step, a third step of soaking the object to be treated after the second step in strongly acidic electrolytic water obtained in the first step, causing air to jet in the strongly acidic electrolytic water, collecting a chlorine gas exhausted from the strongly acidic electrolytic water and causing the collected chlorine gas to jet in the strongly acidic electrolytic water and a fourth step of neutralizing the strongly alkaline electrolytic water after the second step with the strongly acidic electrolytic water after the third step.

The third sterilization method according to the present invention cleans the object to be treated with the strongly alkaline electrolytic water and thereby facilitates cleaning of contamination with protein such as blood that coagulates under an acidic condition. Next, cleaning with strongly acidic electrolytic water can sterilize the object to be treated. By causing a gas to jet in this case, it is possible to peel away bacteria and contamination stuck to the object to be treated and thereby improve the sterilization effect. By neutralizing strongly alkaline electrolytic water used for treatment with the strongly acidic electrolytic water used for treatment, it is possible to discard treated water with safe pH, avoid damage to piping and reduce a burden on the environment.

In the first to third sterilization method according to the present invention, jetting of a gas is preferably conducted by sending 0.1 to 100 L/minute of air. According to the present invention, the object to be treated can be anything to be sterilized and can be food as well as medical equipment such as an endoscope.

In the first to third sterilization methods according to the present invention, the air may be heated air. Furthermore, the chlorine gas may be a heated chlorine gas. The temperature of the heated air or chlorine gas is preferably within a range of 30° C. to 45° C. and more preferably within a range of 40° C. to 45° C. In this case, the sterilization effect can be enhanced by a synergetic effect between the strongly acidic electrolytic water and heating.

In the first to third sterilization methods according to the present invention, the chlorine gas exhausted from the strongly acidic electrolytic water is collected and the collected chlorine gas is made to jet in the strongly acidic electrolytic water, and therefore it is possible to increase the effective chlorine concentration and improve the sterilization effect.

A sterilization processing apparatus according to the present invention is characterized by including a reservoir provided with an anode chamber and a cathode chamber, the anode chamber and the cathode chamber each being provided with a drain having an on-off-valve, an electrolysis apparatus which electrolyzes water in the reservoir, generates strongly acidic electrolytic water in the anode chamber and generates strongly alkaline electrolytic water in the cathode chamber, a first wash container provided with a drain having an on-off valve for receiving and retaining the strongly alkaline electrolytic water from the drain of the cathode chamber, a hermetically sealable second wash container provided with a drain having an on-off valve for receiving and retaining strongly acidic electrolytic water from the drain of the anode chamber, a gas jetting apparatus provided with a collector pipe communicating with the inside of the second wash container for causing air or the chlorine gas collected from the inside of the second wash container through the collector pipe to jet in the strongly acidic electrolytic water inside the second wash container, and a waste water container for receiving waste water from the drain of the first wash container and the drain of the second wash container.

In the sterilization processing apparatus according to the present invention, the gas jetting apparatus may also include a heating apparatus which heats the collected chlorine gas or the air. In this case, by causing the chlorine gas or air heated in the strongly acidic electrolytic water to jet and through a synergetic effect between the strongly acidic electrolytic water and heating, it is possible to enhance the sterilization effect. The temperature of the chlorine gas or air heated by the heating apparatus is preferably within a range of 30° C. to 45° C. and more preferably within a range of 40° C. to 45° C.

In the sterilization processing apparatus according to the present invention, by collecting the chlorine gas exhausted from the strongly acidic electrolytic water and causing the collected chlorine gas to jet in the strongly acidic electrolytic water, it is possible to increase concentration of effective chlorine and enhance the sterilization effect. The electrolysis apparatus may or may not have a diaphragm.

The sterilization processing apparatus according to the present invention is suitable for implementation of the third sterilization method according to the present invention.

The following testing was conducted to observe sterilization effects of the strongly acidic electrolytic water according to the present invention.

First, using an electrolysis apparatus with a diaphragm, a 10 mM saline solution was subjected to electrolysis at a voltage of 12 V, a current of 0.8 A to generate strongly acidic electrolytic water of pH 2 to 4. 300 mL of the strongly acidic electrolytic water generated was put into a beaker, 10 L/minute of air was sent to cause the air to jet using an air pump, 990 µL of the strongly acidic electrolytic water 1 minute, 3 minutes, 5 minutes and 10 minutes after the jetting was started was extracted and mixed with 10 µL of bacterial culture, and the sterilization effect was evaluated. Table 4 shows the type of bacteria used for the testing and the result thereof.

TABLE 4

| | pH | $Cl_2$ [mg/L] | S. aureus | E. coli | P. aeruginosa |
|---|---|---|---|---|---|
| pre | 2.10 (25.9° C.) | 90 | <5 sec. <5 sec. | <5 sec. <5 sec. | <5 sec. <5 sec. |
| 1 min. | 2.20 (26.2° C.) | 75 | <5 sec. <5 sec. | <5 sec. <5 sec. | <5 sec. <5 sec. |
| 3 min. | 2.22 (26.3° C.) | 60 | <5 sec. <5 sec. | <5 sec. <5 sec. | <5 sec. <5 sec. |
| 5 min. | 2.22 (26.3° C.) | 45 | <5 sec. <5 sec. | <5 sec. <5 sec. | <5 sec. <5 sec. |
| 10 min. | 2.23 (26.1° C.) | 25 | >60 sec. >60 sec. | <15 sec. <5 sec. | <5 sec. <5 sec. |

It is appreciated from the result of Table 4 that the strongly acidic electrolytic water generated has the effect of sterilization in a short time with the jetting of air.

The following testing was conducted to observe sterilization effects when using a carrier of the strongly acidic electrolytic water according to the present invention.

First, using an electrolysis apparatus with a diaphragm, a 10 mM saline solution was subjected to electrolysis at a voltage of 12 V, a current of 0.8 A to generate strongly acidic electrolytic water of pH 2 to 4. 300 mL of the strongly acidic electrolytic water generated was put into a beaker, 10 carriers containing staphy lococcusaureus were put therein, 10 L/minute of air was sent to cause the air to jet using an air pump and the number of carriers where bacteria remained was calculated five minutes after the jetting was started. In a comparative example, the number of carriers where bacteria remained was calculated five minutes after without jetting air. Table 5 shows the result together with pH of the strongly acidic electrolytic water used for the testing.

Furthermore, Table 6 shows the results in a case where the stirring was continued with a medium degree of intensity instead of jetting air and in a case where the stirring was continued with a high degree of intensity.

TABLE 5

| | Aeration | | | Without aeration | | |
|---|---|---|---|---|---|---|
| | pH | $Cl_2$ | carrier | pH | $Cl_2$ | Carrier |
| First time | 2.32(26.7° C.) | 70 | | | | |
| 5 minutes later | 2.22(26.5° C.) | 28 | 1/10 | 2.26 (26.8° C.) | 55 | 8/10 |
| Second time | 2.27(26.9° C.) | 100 | | | | |
| 5 minutes later | 2.15(26.6° C.) | 28 | 5/10 | 2.11 (27.1° C.) | 70 | 10/10 |
| Third time | 2.27(26.6° C.) | 95 | | | | |
| 5 minutes later | 2.20(26.4° C.) | 32 | 1/10 | 2.20 (26.8° C.) | 70 | 10/10 |

TABLE 6

| | Middle stirring | | | High stirring | | |
|---|---|---|---|---|---|---|
| | pH | $Cl_2$ | carrier | pH | $Cl_2$ | Carrier |
| First time | 2.33(26.2° C.) | 90 | | | | |
| 5 minutes later | | | 1/10 | | | 0/10 |
| Second time | 2.37(26.0° C.) | 100 | | | | |
| 5 minutes later | 2.28(26.1° C.) | 75 | 0/10 | 2.36 (25.9° C.) | 55 | 2/10 |
| Third time | 2.33(26.2° C.) | 100 | | | | |
| 5 minutes later | 2.37(26.1° C.) | 80 | 0/10 | 2.38 (25.8° C.) | 35 | 0/10 |

It is appreciated from the result in Table 5 that a higher sterilization effect can be obtained when five-minute air jetting was conducted than when no air jetting was applied. It is appreciated from the result in Table 6 that it is possible to obtain a high sterilization effect also in the case where stirring continued with a medium degree of intensity or a high degree of intensity as well as the case where air jetting was applied.

Thus, introducing the air jetting processing method according to the present invention can shorten the sterilization duration and at the same time enhance the sterilization effect. Increasing the sterilizing power prevents emission of a chlorine gas and provides a new environmentally-friendly technique.

High concentration of effective chlorine dissolved in strongly acidic electrolytic water is generally considered as a defect of strongly acidic electrolytic water and causes corrosion of piping or the like, but shortening the air jetting processing time can prevent corrosion. Furthermore, jetting the air and emitting the chlorine gas from strongly acidic electrolytic water into the air can reduce influences of strongly acidic electrolytic water on corrosion.

According to the present invention, the strongly acidic electrolytic water can be obtained by electrolyzing a 1.0 mM concentration saline solution at a voltage of 12 V and a current of 0.8 A for 15 minutes, for example. FIG. 1 shows the reaction process thereof.

The present invention can provide a sterilization method and sterilization processing apparatus having a high sterilization effect and capable of shortening a sterilization time.

BRIEF DESCRIPTION OF THE DRAWINGS

FIG. 1 illustrates a reaction process of strongly acidic electrolytic water according to an embodiment of the present invention;

DETAILED DESCRIPTION OF THE PREFERRED EMBODIMENTS

Hereinafter, an embodiment of the present invention will be explained with reference to the attached drawings.

Figure 2:
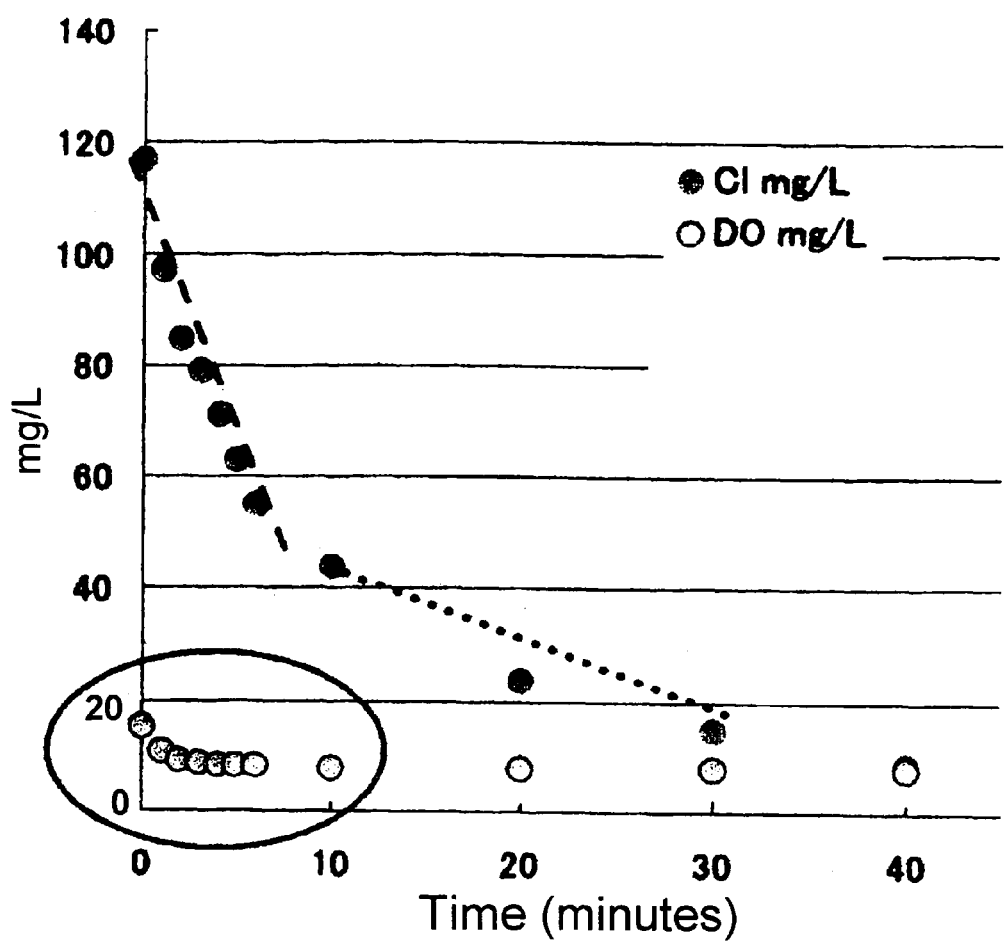
FIG. 2 is a graph showing a temporal variation in concentration of effective chlorine dissolved in strongly acidic electrolytic water and concentration of dissolved oxygen with jetting of air according to the present invention.
Figure 3:
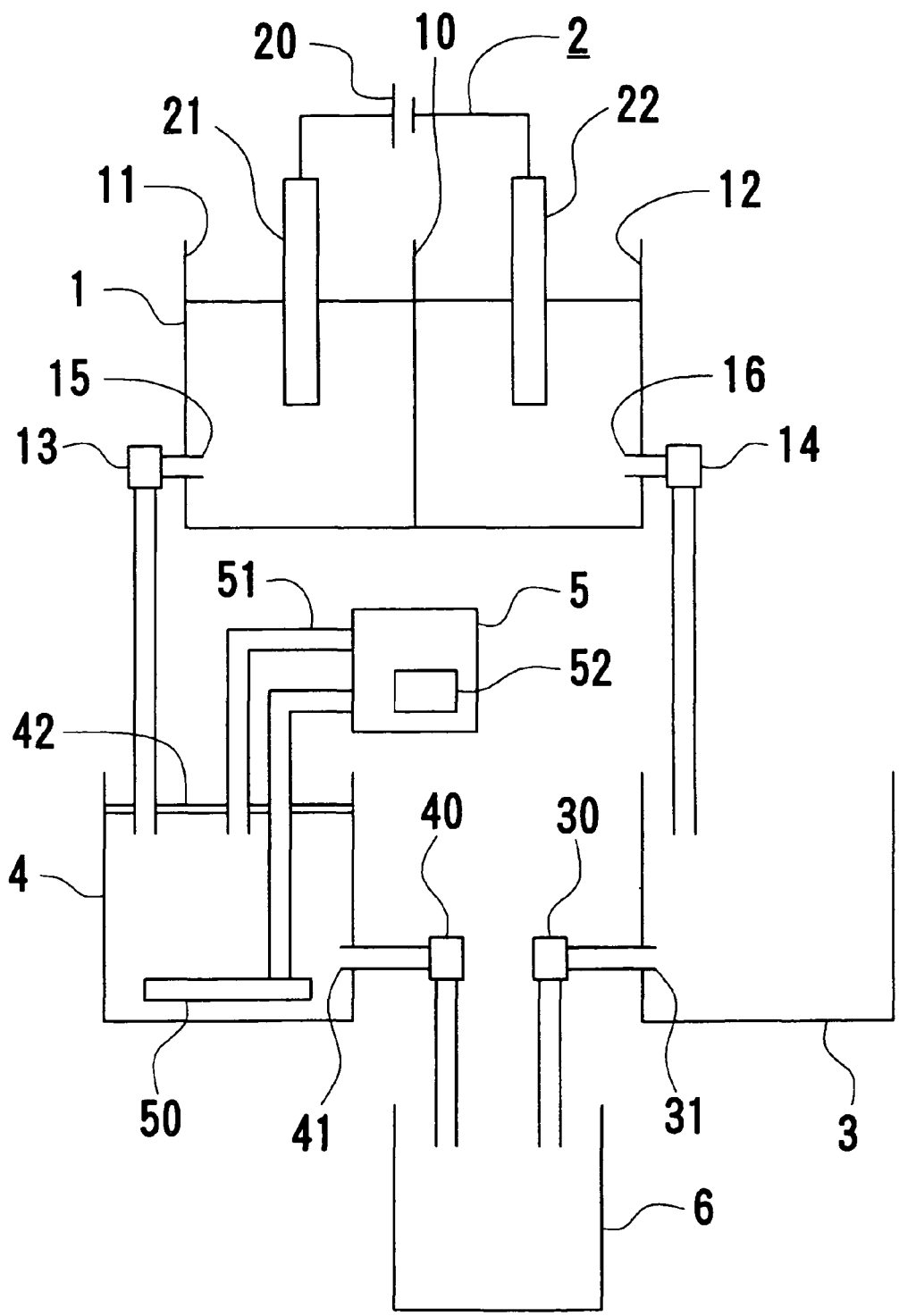
FIG. 3 schematically illustrates the configuration of a sterilization processing apparatus according to the present invention.

FIG. 3 shows a sterilization processing apparatus according to an embodiment of the present invention.

As shown in FIG. 3, the sterilization processing apparatus has a reservoir 1, electrolysis apparatus 2, first wash container 3, second wash container 4, gas jetting apparatus 5 and waste water container 6.

The reservoir 1 is provided with an anode chamber 11 and cathode chamber 12 partitioned by a diaphragm for electrolysis 10. The anode chamber 11 and cathode chamber 12 are each provided with drains 15 and 16 having on-off valves 13 and 14. The electrolysis apparatus 2 has an anode 21 and cathode 22, places the anode 21 in the anode chamber 11 and the cathode 22 in the cathode chamber 12. The electrolysis apparatus 2 is connected to a power supply 20, electrolyzes water in the reservoir 1, generates strongly acidic electrolytic water in the anode chamber 11 and generates strongly alkaline electrolytic water in the cathode chamber 12.

The first wash container 3 is a container to retain strongly alkaline electrolytic water of the cathode chamber 12 and is provided with a drain 31 having an on-off valve 30. The second wash container 4 is a container to retain strongly acidic electrolytic water of the anode chamber 11 and is provided with a drain 41 having an on-off valve 40. The second wash container 4 has a cover 42 and can be hermetically sealed.

The gas jetting apparatus 5 has a gas jetting part 50 disposed at the bottom of the second wash container 4 so as to supply a gas to the strongly acidic electrolytic water in the second wash container 4. The gas jetting apparatus 5 has a collector pipe 51 communicating with the inside of the second wash container 4 lower than the cover 42. The gas jetting apparatus 5 can jet the chlorine gas collected from the inside of the second wash container 4 through the collector pipe 51 into the strongly acidic electrolytic water from the gas jetting part 50.

Incidentally, the collector pipe 51 may also be left open to the atmosphere instead of communicating with the inside of the second wash container 4. In this case, the air outside the second wash container 4 can be jetted from the gas jetting part 50.

The gas jetting apparatus 5 has a heating apparatus 52 designed to be able to heat the chlorine gas or air collected through the collector pipe 51 and jet the heated chlorine gas or air from the gas jetting part 50.

The waste water container 6 is designed to receive waste water from the drain 31 of the first wash container 3 and the drain 41 of the second wash container 4.

Next, the operation will be explained.

The sterilization processing apparatus shown in FIG. 3 is suitably used to clean an endoscope or the like.

First, water is retained in the reservoir 1, salt is added to make a 10 mM saline solution and this saline solution is subjected to electrolysis through the electrolysis apparatus 2 at a voltage of 12 V and a current of 0.8 A. Electrolysis is continued for approximately 15 minutes, strongly acidic electrolytic water of pH 2 to 4 is generated in the anode chamber 11 and strongly alkaline electrolytic water of pH 10 to 12 is generated in the cathode chamber 12.

The on-off valve 14 of the cathode chamber 12 is opened, strongly alkaline electrolytic water is introduced from the drain 16 into the first wash container 3, the on-off valve 13 of the anode chamber 11 is opened and strongly acidic electrolytic water is introduced from the drain 15 into the second wash container 4. An object to be treated (e.g., endoscope) is placed in the first wash container 3 and cleaned with the strongly alkaline electrolytic water. Cleaning the object to be treated with the strongly alkaline electrolytic water facilitates cleaning of contamination of protein such as blood which coagulates under an acidic condition.

The object to be treated cleaned with the strongly alkaline electrolytic water is placed in the second wash container 4 and soaked in strongly acidic electrolytic water. Cleaning with the strongly acidic electrolytic water can sterilize the object to be treated. The gas jetting apparatus 5 is activated to cause a gas to jet from the gas jetting part 50 in the strongly acidic electrolytic water. Jetting the gas can peel away bacteria or contamination stuck to the object to be treated with a pressure and enhance the sterilization effect.

After gas jetting, the gas exited from the strongly acidic electrolytic water is sent from the collector pipe 51 of the gas jetting apparatus 5 to the gas jetting part 50 and jetted in the strongly acidic electrolytic water again. The gas jetted in the strongly acidic electrolytic water can be heated to 30° C. to 45° C. by the heating apparatus 52. When heated, the synergetic effect between the strongly acidic electrolytic water and heating can enhance the sterilization effect.

After cleaning of the object to be treated, the strongly alkaline electrolytic water remaining in the first wash container 3 is moved from the drain 31 to the waste water container 6 through the on-off valve 30 which is opened and then after cleaning of the object to be treated, the strongly acidic electrolytic water remaining in the second wash container 4 is moved from the drain 41 to the waste water container 6 through the on-off valve which is opened. In this way, neutralizing the strongly alkaline electrolytic water used for treatment with the strongly acidic electrolytic water used for treatment can discard the treated water with safe pH, avoid damage to the piping and also reduce a burden on the environment.

What is claimed is:

1. A sterilization method comprising the steps of:
soaking an object to be treated in strongly acidic electrolytic water of pH 2 to 4 obtained by electrolyzing an aqueous solution of chloride and causing air to jet in the strongly acidic electrolytic water;
collecting a chlorine gas exhausted from the strongly acidic electrolytic water, the chlorine gas being heated; and
causing the collected chlorine gas to jet inside the strongly acidic electrolytic water, wherein
the entire jetted substance is a gas, and the temperature of the heated chlorine gas is 30° C. to 45° C.

2. A sterilization method comprising the steps of:
soaking an object to be treated in strongly acidic electrolytic water of pH 2 to 4 obtained by electrolyzing an aqueous solution of chloride and stirring the aqueous solution of chloride;
collecting a chlorine gas exhausted from the strongly acidic electrolytic water; and
causing the collected chlorine gas to jet in the strongly acidic electrolytic water, wherein
the entire jetted substance is a gas, and the collected chlorine gas is heated to a temperature between 30° C. to 45° C.

3. A sterilization method comprising:
a first step of electrolyzing an aqueous solution of chloride and generating strongly acidic electrolytic water and strongly alkaline electrolytic water;
a second step of cleaning an object to be treated with the strongly alkaline electrolytic water obtained in the first step;
a third step of soaking the object to be treated after the second step in the strongly acidic electrolytic water obtained in the first step, causing air to jet in the strongly acidic electrolytic water, collecting a chlorine gas exhausted from the strongly acidic electrolytic water and causing the collected chlorine gas to jet in the strongly acidic electrolytic water; and
a fourth step of neutralizing the strongly alkaline electrolytic water after the second step with the strongly acidic electrolytic water after the third step, wherein
the entire jetted substance is a gas, and the collected chlorine gas is heated to a temperature between 30° C. to 45° C.

4. The sterilization method according to claim 1, wherein the air is heated air.

5. The sterilization method according to claim 4, wherein the temperature of the heated air is 30° C. to 45° C.

6. A sterilization processing apparatus comprising:
a reservoir provided with an anode chamber and a cathode chamber, the anode chamber and the cathode chamber each being provided with a drain having an on-off valve;
an electrolysis apparatus that: electrolyzes water in the reservoir, generates strongly acidic electrolytic water in the anode chamber and generates strongly alkaline electrolytic water in the cathode chamber;
a first wash container provided with a drain having an on-off valve for receiving and retaining the strongly alkaline electrolytic water from the drain of the cathode chamber;
a hermetically sealable second wash container provided with a drain having an on-off valve for receiving and retaining strongly acidic electrolytic water from the drain of the anode chamber;
a gas jetting apparatus provided with a collector pipe communicating with the inside of the second wash container for causing air or the chlorine gas collected from the inside of the second wash container through the collector pipe to jet in the strongly acidic electrolytic water inside the second wash container; and
a waste water container for receiving waste water from the drain of the first wash container and the drain of the second wash container, wherein
the entire jetted substance is a gas, and the gas jetting apparatus is provided with a heating apparatus to heat the collected chlorine gas to a temperature between 30° C. to 45° C.

7. The sterilization processing apparatus according to claim 6, wherein the heating apparatus also heats the air.

8. The sterilization method according to claim 3, wherein the air is heated air.

9. The sterilization method according to claim 8, wherein the temperature of the heated air is 30° C. to 45° C.

10. The sterilization method according to claim 7, wherein the temperature of the heated air is 30° C. to 45° C.

11. The sterilization method according to claim 2, wherein the air is heated air.

12. The sterilization method according to claim 11, wherein the temperature of the heated air is 30° C. to 45° C.

* * * * *